US008757151B2

(12) United States Patent
Johnstone et al.

(10) Patent No.: US 8,757,151 B2

(45) Date of Patent: Jun. 24, 2014

(54) HEADGEAR-MOUNTABLE RESPIRATOR

(75) Inventors: Clive Johnstone, Abingdon (GB); Stephen Hare, Garsington (GB)

(73) Assignee: JSP Limited, Oxfordshire (GB)

( * ) Notice: Subject to any disclaimer, the term of this patent is extended or adjusted under 35 U.S.C. 154(b) by 543 days.

(21) Appl. No.: 13/117,746

(22) Filed: May 27, 2011

(65) Prior Publication Data

US 2012/0024289 A1 Feb. 2, 2012

Related U.S. Application Data

(60) Provisional application No. 61/368,772, filed on Jul. 29, 2010.

(51) Int. Cl.
*A61M 11/00* (2006.01)

(52) U.S. Cl.
USPC .................. 128/204.18; 417/350; 417/423.14

(58) Field of Classification Search
CPC ................. A61M 16/0066; A61M 2016/0039; A61M 16/06
USPC ............. 128/204.18, 204.23, 204.28, 204.21; 417/350, 423.14
See application file for complete search history.

(56) References Cited

U.S. PATENT DOCUMENTS

| | | | | |
|---|---|---|---|---|
| 4,430,995 | A * | 2/1984 | Hilton | 128/204.21 |
| 5,372,130 | A * | 12/1994 | Stern et al. | 128/205.25 |
| 5,533,500 | A * | 7/1996 | Her-Mou | 128/201.25 |
| 6,158,978 | A * | 12/2000 | Norbury, Jr. | 417/350 |
| 6,435,184 | B1 * | 8/2002 | Ho | 128/206.21 |
| 6,896,478 | B2 * | 5/2005 | Botros et al. | 415/101 |
| 8,517,012 | B2 * | 8/2013 | Daly et al. | 128/204.18 |
| 2004/0079373 | A1 | 4/2004 | Mukaiyama et al. | |

* cited by examiner

*Primary Examiner* — Steven Douglas
(74) *Attorney, Agent, or Firm* — Keith Swedo

(57) ABSTRACT

A headgear-mountable respirator (100) including a first intake (106A) and first associated impeller (108A), as well as a second intake (106B) and second associated impeller (108B) located remotely from the first intake and the first impeller. The respirator further includes a device (112) for, in use, rotating at least one of the impellers, and an air delivery arrangement (103A, 103B) for, in use, delivering air drawn from the first and second intakes to a facial region of a user.

16 Claims, 7 Drawing Sheets

HEADGEAR-MOUNTABLE RESPIRATOR

The present application claims priority from U.S. provisional Ser. No. 61/368,772 filed on Jul. 29, 2010.

FIELD OF THE INVENTION

The present invention relates to headgear-mountable respirators.

BACKGROUND TO THE INVENTION

Respirators are available that fit onto safety helmets and the like. These typically include a motor that draws air from a single intake using an impeller and then directs it towards the user's face or breathing mask. Existing respirators have a convoluted path between the motor and the intake, which reduces efficiency and means that a powerful motor has to be used. This increases product weight and footprint, which is undesirable in head-mounted apparatus.

Another problem associated with conventional head-mounted respirators is that the respirator needs to be securely fixed to the helmet. This means that it is inconvenient and difficult to remove the respirator for maintenance or replacement. On the other hand, if the connection between the respirator and the helmet is not sufficiently strong then there is a risk of the respirator falling off, resulting in risks to the user and damage to the apparatus.

SUMMARY OF THE INVENTION

Embodiments of the present invention address at least some of the problems discussed above.

According to a first aspect of the present invention there is provided a headgear-mountable respirator including:

a first intake and first associated impeller;

a second intake and second associated impeller located remotely from the first intake and the first impeller;

a device for, in use, rotating at least one of the impellers, and an air delivery arrangement for, in use, delivering air drawn from the intakes to a facial region of a user.

The second intake may be opposed to the first intake.

The first impeller and the second impeller may have a common axis.

The rotating device will typically rotate the first and the second impellers.

The rotating device may be located between the first impeller and the second impeller. The rotating device may comprise a motor with a through-shaft. The respirator may include a central conduit between the first impeller and the second impeller and the rotating device may be located in the central conduit.

The air delivery arrangement may include a first conduit leading from the first impeller toward the facial region and a second conduit leading from the second impeller toward the facial region. The first (and/or the second) conduit may be transverse to the axis of the first (and/or the second) impeller, e.g. the conduit may be substantially perpendicular to the axis.

The air delivery arrangement may direct at least some of the air drawn from the intakes towards a visor portion of the headgear item, thereby providing a de-misting function.

A (removable) filter may be fitted to the first (and/or the second) intake.

The respirator may be directly or indirectly mounted on a peak portion of a headgear item. The respirator may be mounted on (or integrated with) a portion that is releasably attached to the peak portion. The releasable portion may have a shape or profile that generally corresponds to a shape or profile of the peak portion. The releasable portion may include at least one formation that, in use, allows the releasable portion to slidably fit into the shape/profile of the peak portion so that the releasable portion is in a fitted configuration, but hinders/prevents removal of the releasable portion from the fitted configuration. The at least one formation may comprise a nub with an angled edge. The nub may be generally triangular in shape.

The first (and/or the second) conduit may lead to/through the peak portion.

At least some components of the respirator may include an explosion proof housing.

According to another aspect of the present invention there is provided headgear, e.g. helmet or cap, including a respirator substantially as described herein.

According to yet another aspect of the present invention there is provided a mounting member adapted to mount a device (e.g. a respirator) on a peak portion of a headgear item, the member including an arrangement for, in use, releasably attaching the member to the peak portion.

According to a further aspect of the present invention there is provided a device, e.g. a respirator, including a mounting member substantially as described herein.

According to yet another aspect of the present invention there is provided a headgear item including a peak portion (or a peak portion for headgear) adapted to receive a mounting member substantially as described herein.

According to another aspect of the present invention there is provided a kit comprising at least one headgear item (or at least one peak portion for a headgear item) and a mounting member (or mounted device) substantially as described herein.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments. As such, many modifications and variations will be apparent to practitioners skilled in the art. Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

BRIEF DESCRIPTION OF THE DRAWINGS

The invention may be performed in various ways, and, by way of example only, embodiments thereof will now be described, reference being made to the accompanying drawings in which.

DETAILED DESCRIPTION OF THE DRAWINGS

Figure 1:
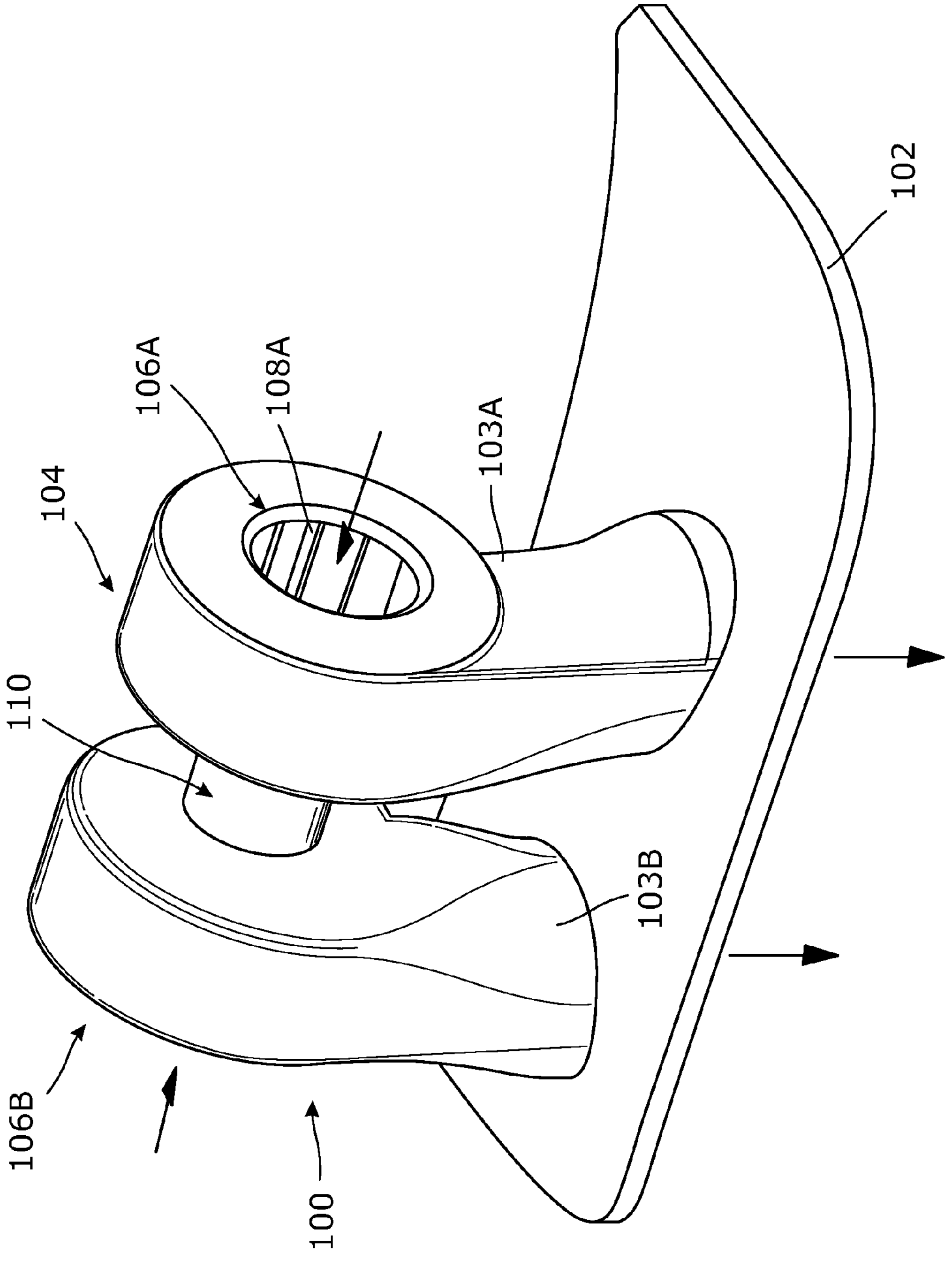
FIG. 1 is a perspective view of components of an example respirator.
Figure 2A:
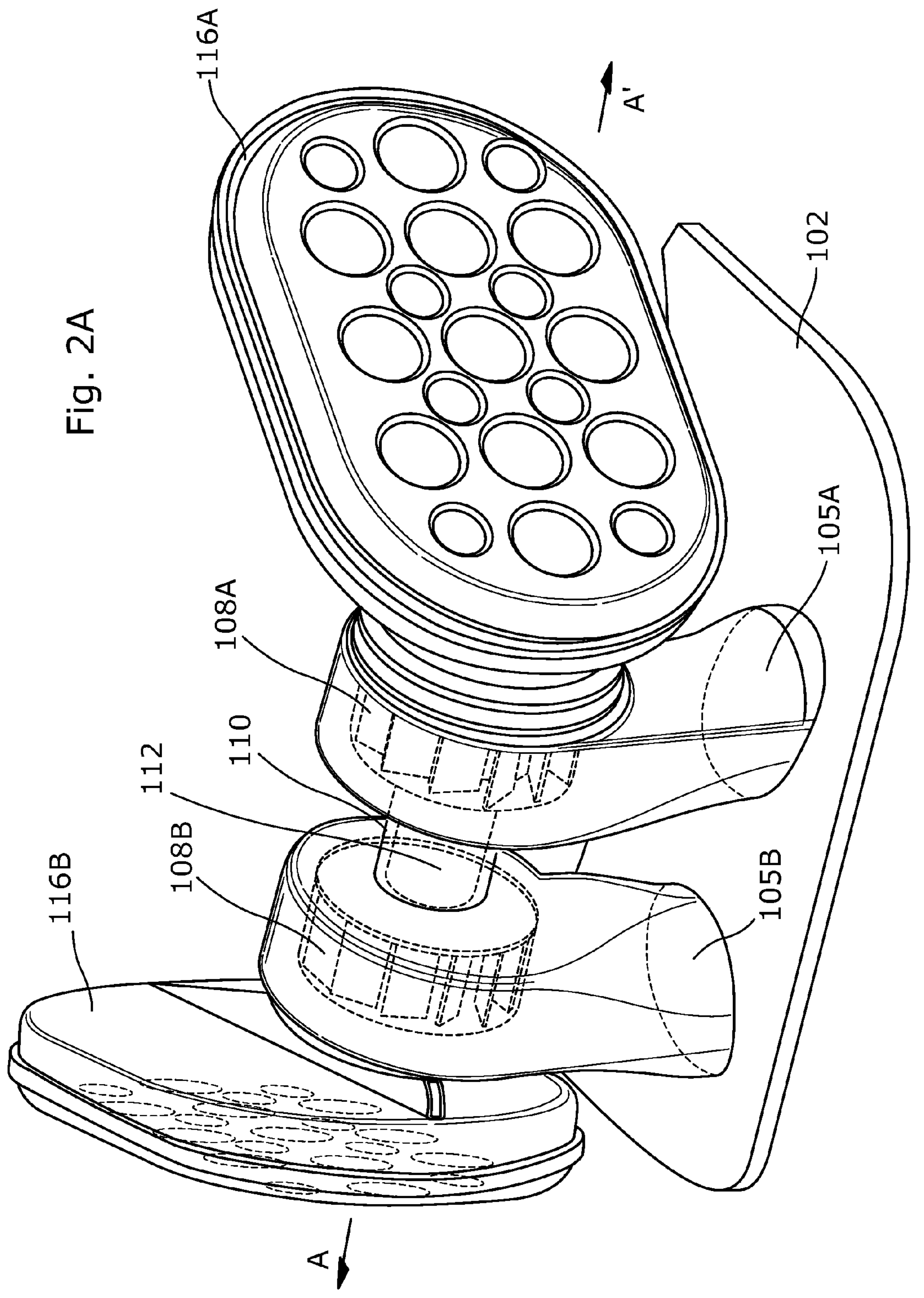
FIG. 2A is a perspective, semi-transparent view of the respirator with filter members fitted.
Figure 2B:
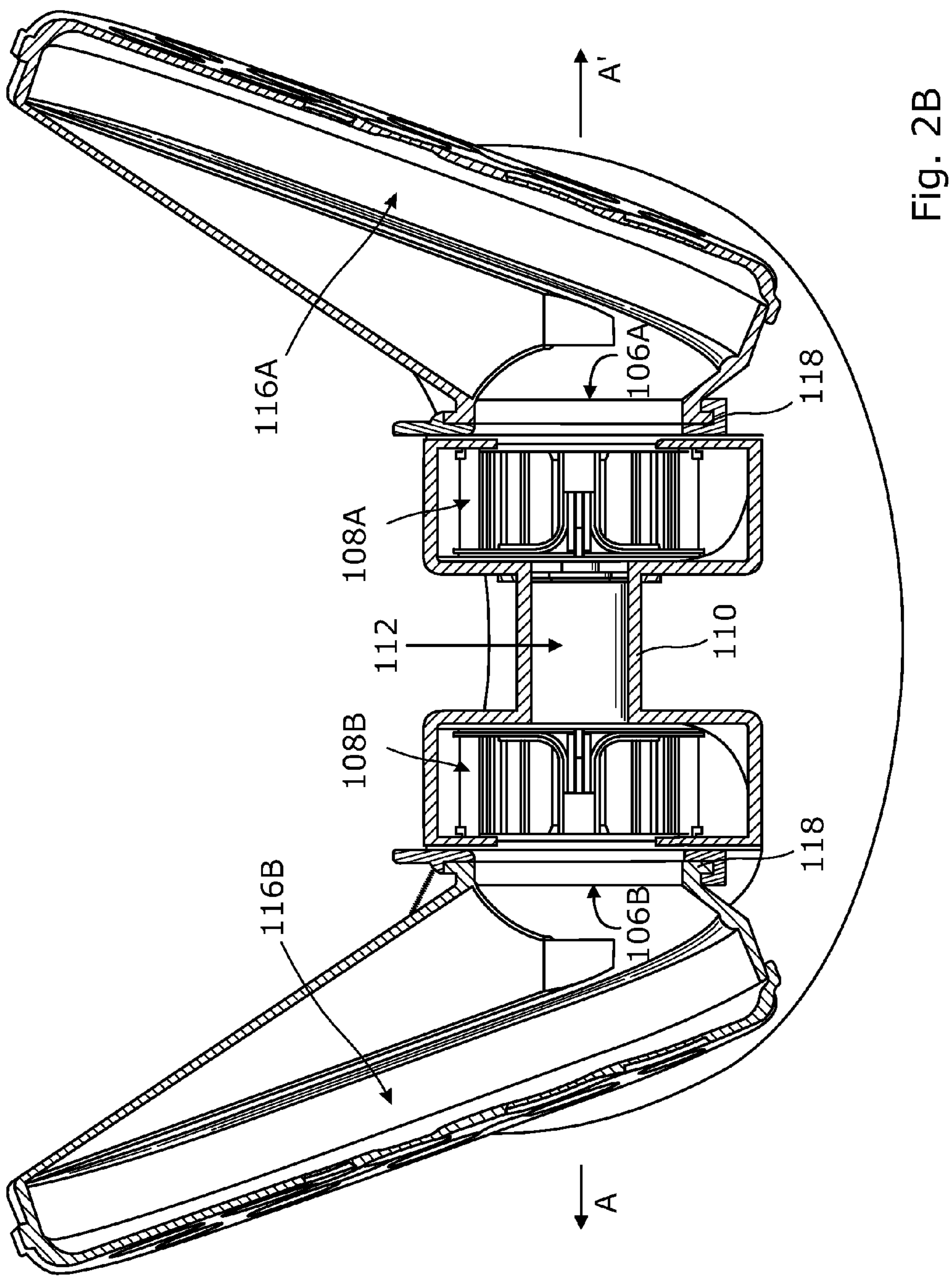
FIG. 2B is a sectional view through line A-A' of FIG. 2A

Referring to FIGS. 1, 2A and 2B, an example respirator 100 is shown. The respirator is fitted to a peak 102 of an item of headgear, such as a safety helmet, or baseball-style safety cap, although it will be understood that these are examples only.

The respirator includes a housing 104, which, in the example, is formed of moulded plastic, although the skilled person will understand that it could be formed of any other suitable material(s). The housing may be formed of explosion proof material that complies with the ATEX standard. The housing forms a first (right-hand in the Figures) conduit portion 103A that includes an intake 106A. The conduit portion has a generally inverted L-shape and leads to an outlet 105A located on/in the peak 102 of the helmet. Example dimensions for the conduit 103A are around 20 mm-50 mm tall×25 mm-35 mm wide×25 mm-35 mm. Fitted within the conduit adjacent the intake 106A is an impeller 108A comprising a set of rotors, although it will be appreciated that other air-drawing/directing mechanisms could be used. Opposite the first conduit 103A, and spaced apart from it, there is a second conduit 103B (left-hand in the Figures). The second conduit is a mirror-image of the first conduit and includes a similar intake 106B, impeller 108B and an outlet 105B in/on the peak.

Between the first and second conduits 103A, 103B there is a central through-shaft 110, which, in the example, takes the form of a cylinder having a length of around 15 mm-35 mm. which means that the overall width of the respirator is 70 mm-110 mm (without the filter shown in FIG. 2A, or 140 mm-250 mm with the filter). Fitted within the through-shaft 110 is a motor 112, such as a Maxon A-Max19. The motor includes spindles 114A, 114B at either side, which, in use, rotate the impellers 108A, 108B simultaneously. Components related to the motor, e.g. operating switches and power source, e.g. battery, are not shown for clarity.

FIGS. 2A and 2B show filter members 116A, 116B fitted onto the intakes 106A, 106B, respectively. The filters are removable and include formations that fit into recesses 118 (best seen in FIG. 2B) in the housing adjacent the intakes 106A, 106B.

The skilled person will appreciate that the design shown in the Figures is exemplary only and variations are possible. For instance, the location and design of the intakes/impellers could be different to those shown (and all of them need not be identical); more than two intakes/impellers could be provided (and separate motors may be used to independently rotate impellers); back-up motors may be provided, and so on.

In use, the motor 112 is activated and rotates the twin impellers 108A, 108B. The action of the impellers draws air into the respirator through the filters 116A, 116B and then down into the outlets 105A, 105B, towards a mouth/nose region of the user (the face shield forms a "plenum" for the air). The flow of air is shown schematically by the large arrows in FIG. 1. The location of the outlets on the peak 102 of the helmet means that at least some of the air passing through the outlets can pass to/over a visor (see FIG. 3) of the helmet, thereby providing a de-misting effect. Having more than one intake means that air can be drawn into the respirator more efficiently than single intake devices. Additionally, the use of a single motor to drive more than one impeller means that this advantage can be provided within a relatively compact device. Having the motor located between two opposed intakes/impellers is particularly efficient and the impellers are also located directly adjacent the intakes and there is only a short distance between the motor and both impellers. Experiments have shown that the airflow can be in the range of around 120 l/min-200 l/min, using 20% less power than respirators having a single impeller.

Figure 3:
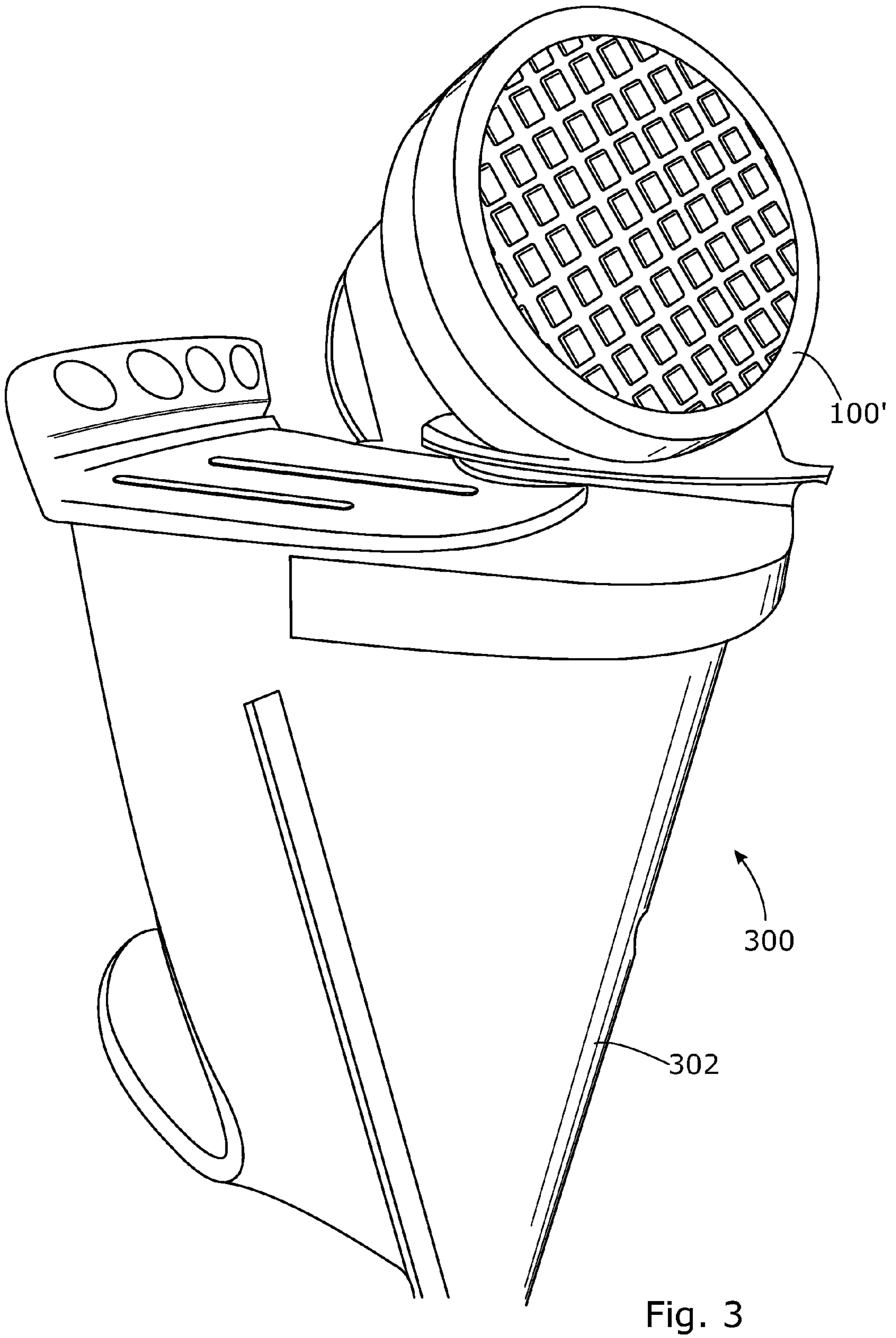
FIG. 3 shows another example respirator fitted to headgear.

FIG. 3 shows a facemask 300 removably fitted under the peak 102 of the helmet. The facemask includes a transparent visor 302. An alternative version of the respirator 100' with only a single outlet 105' is shown in the Figure.

Figure 4:
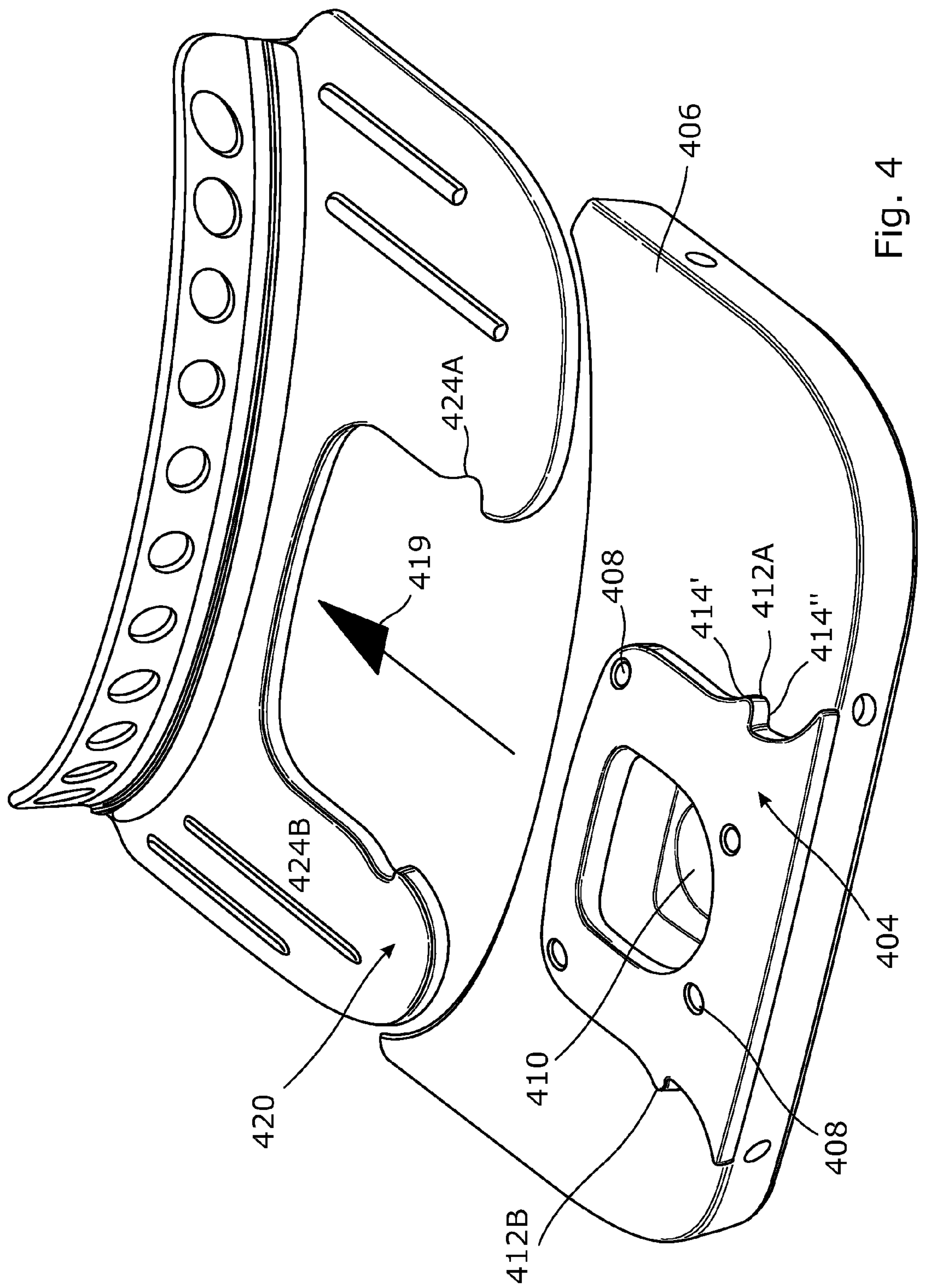
FIG. 4 shows a member upon which a device, such as a respirator, can be mounted and releasable fitted into the peak of the headgear.

FIG. 4 shows a member 402 that can be used to releasably fit the respirator 100' on the helmet peak 102. The member 402 is shown having a base plate 404 that can form part of, or be fitted to, the lower portion of the respirator that includes the outlet(s). In the example the plate 404 is attached to an existing visor carrier 406 by means of screws 408, although it will be understood that other fixing means could be used.

The member 402 includes an aperture 410 for allowing flow communication with the outlet of the respirator and the mouth/nose region of the user. The opposed side edges of the base plate 404 include nubs 412A, 412B. Each of the nubs include an angled edge 414' that projects outwardly and another edge 414" that extends back towards the main side edge of the base plate and so each nub is generally triangular in shape. Towards the bottom edge (an edge at the front of the visor in use) there are sweeping, curved formations 416 at both sides.

Figure 5:
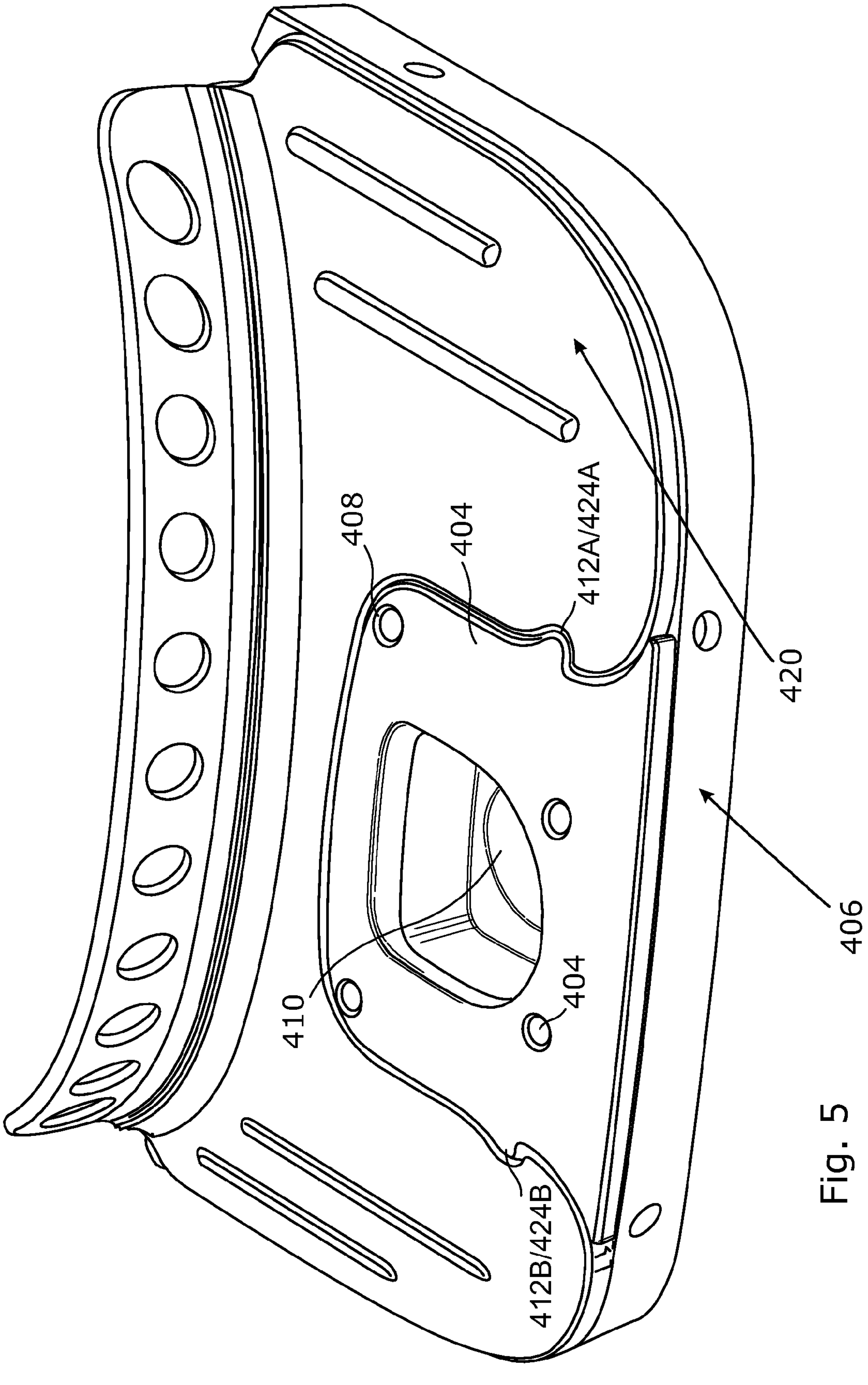
FIG. 5 shows the member fitted into the peak.

The headgear peak component 420 in use is attached to headgear, e.g. by means of stitching, studs, adhesives, etc, (although in other embodiments it may be an integral part of the helmet). The peak component 420 includes a cut-out portion 422 having a profile that generally corresponds to the outline of the base plate 404. The profile includes two side formations 424A, 424B that correspond to the shape of the nubs 412A, 412B on the plate. Thus, when the plate is slid (see arrow 419 and FIG. 5) into the cut-out portion 422, the nubs snap-fit into the side formations and prevent/inhibit movement in the opposite direction. The modular peak 420 is formed of a rigid plastic but has sufficient flexibility to allow the plate to be released when the rear portion (adjacent the user's head) is bent. In other embodiments, the peak may include formations, e.g. two short upstanding portions, that assist the user with "spreading" the peak apart to release the base plate.

Figure 6:
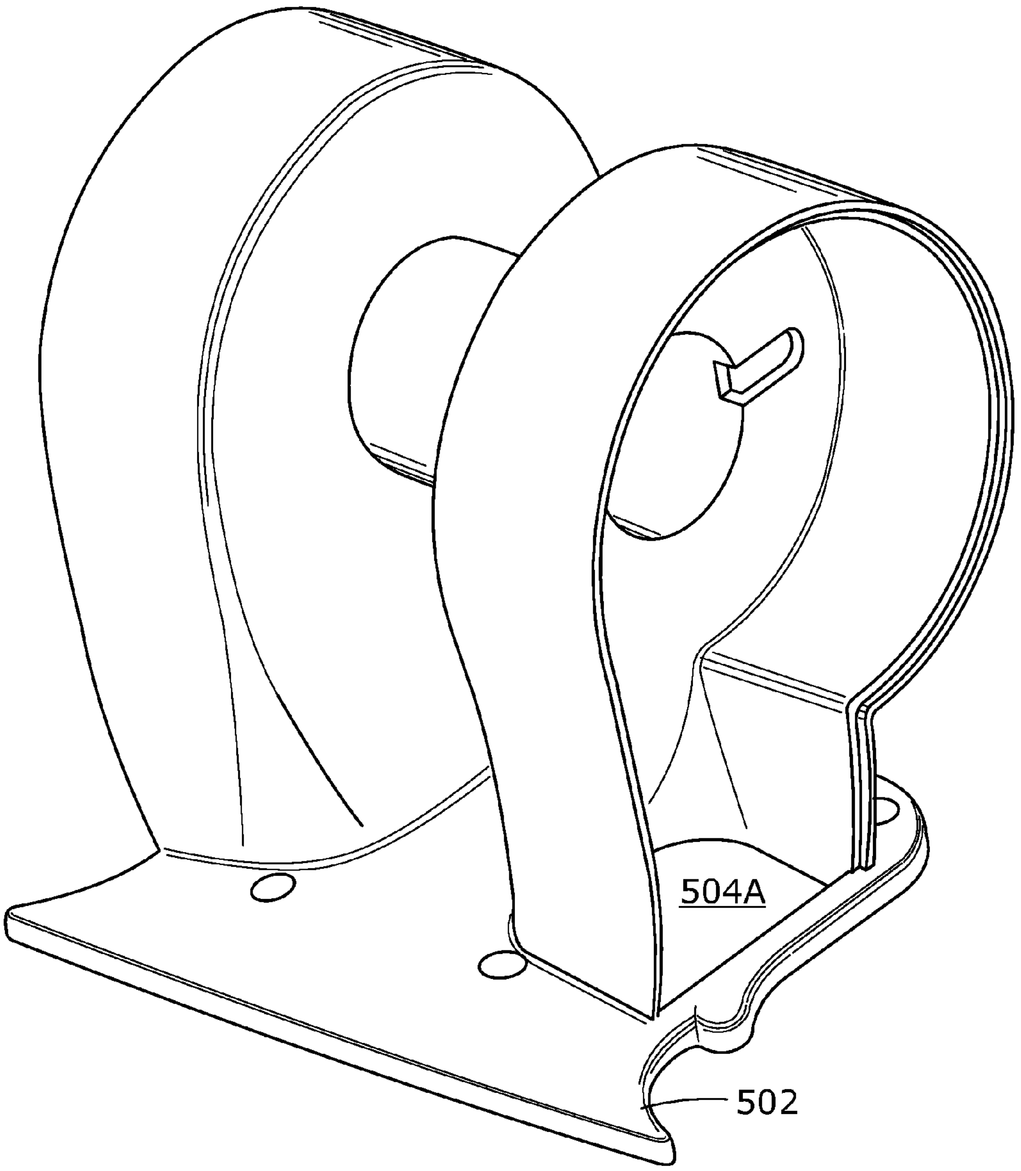
FIG. 6 shows an alternative example respirator mounted on the mounting member.

FIG. 6 shows an alternative embodiment of the base plate 502 where parts of the respirator 100 (corresponding to conduits 103A, 103B) are integrated with the plate. In this case, there are two apertures (only one, 504A, visible), one for each conduit.

The removable components shown in the Figures allow the respirator to be removed easily for maintenance, etc, and then conveniently replaced (without the need for tools such as screwdrivers), whilst providing a secure connection. It also means that peak components can be provided for different items of headgear, allowing the same respirator to be fitted to different items, thereby reducing the amount of respirators that need to be purchased. The skilled person will appreciate that the design and dimensions of the removable components shown are exemplary only and variations are possible. For instance, the formations could be different in location, number and design to the opposed nubs 412, e.g. pivotable/moveable parts may be used to provide the releasable connection.

We claim:

1. A headgear-mountable respirator (100) including:

a first intake (106A) and first associated impeller (108A);

a second intake (106B) and second associated impeller (108B) located remotely from the first intake and the first impeller;

a device (112) for, in use, rotating at least one of the impellers, and an air delivery arrangement (103A, 103B) for, in use, delivering air drawn from the first and second intakes to a facial region of a user, the air delivery arrangement including a first conduit (103A) leading from the first impeller (108A) toward the facial region and a second conduit (103B) leading from the second impeller (108B) toward the facial region, wherein the first (103A) and/or the second (103B) conduit is/are transverse to an axis of the first (108A) and/or the second (108B) impeller.

2. A respirator according to claim 1, wherein the second intake (106B) is opposed to the first intake (106A).

3. A respirator according to claim 2, wherein the first impeller (108A) and the second impeller have a common axis.

4. A respirator according to claim 1, wherein the rotating device (112) rotates both the first (108A) and the second (108B) impellers.

5. A respirator according to claim 4, wherein the rotating device (112) is located between the first (108A) impeller and the second (108B) impeller.

6. A respirator according to claim 5, including a central conduit (110) between the first (108A) and the second (108B) impeller, the rotating device (112) being located in the central conduit.

7. A respirator according to claim 1, wherein first and second conduits (103A, 103B) are substantially perpendicular to the axes.

8. A headgear-mountable respirator (100) including:

a first intake (106A) and first associated impeller (108A);

a second intake (106B) and second associated impeller (108B) located remotely from the first intake and the first impeller;

a device (112) for, in use, rotating at least one of the impellers, and an air delivery arrangement (103A, 103B) for, in use, delivering air drawn from the first and second intakes to a facial region of a user, wherein the air delivery arrangement (103) directs at least some of the air drawn from the intakes (106) towards a visor portion of the headgear item, thereby providing a de-misting function.

9. A respirator according to claim 1, further including a removable filter (118) fitted to the first (106A) and/or the second (106B) intake.

10. A respirator according to claim 1, wherein the respirator (100) is directly or indirectly mounted on a peak portion (420) of a headgear item.

11. A respirator according to claim 10, wherein the respirator (100) is mounted on (or integrated with) a releasable portion (404) that is releasably attached to the peak portion (420).

12. A respirator according to claim 11, wherein the releasable portion (404) has a shape or profile that generally corresponds to a shape or profile (424) in the peak portion (420).

13. A respirator according to claim 12, wherein the releasable portion (404) includes at least one formation (412) that, in use, allows the releasable portion to slidably fit into the shape/profile of the peak portion so that the releasable portion is in a fitted configuration, but hinders/prevents removal of the releasable portion from the fitted configuration.

14. A respirator according to claim 13, wherein the at least one formation comprises a nub (412) with an angled edge (414').

15. A headgear-mountable respirator (100) including:

a first intake (106A) and first associated impeller (108A);

a second intake (106B) and second associated impeller (108B) located remotely from the first intake and the first impeller;

a device (112) for, in use, rotating at least one of the impellers, and an air delivery arrangement (103A, 103B) for, in use, delivering air drawn from the first and second intakes to a facial region of a user, wherein:

the respirator (100) is directly or indirectly mounted on a peak portion (420) of a headgear item;

the respirator (100) is mounted on (or integrated with) a releasable portion (404) that is releasably attached to the peak portion (420);

the releasable portion (404) has a shape or profile that generally corresponds to a shape or profile (424) in the peak portion (420);

the releasable portion (404) includes at least one formation (412) that, in use, allows the releasable portion to slidably fit into the shape/profile of the peak portion so that the releasable portion is in a fitted configuration, but hinders/prevents removal of the releasable portion from the fitted configuration;

the at least one formation comprises a nub (412) with an angled edge (414'); and the nub (412) is generally triangular in shape, and at least some components of the respirator include an explosion proof housing (104).

16. A headgear item including a respirator according to claim 1, including a mounting member (404) adapted to mount the respirator on a peak portion of the headgear item, the mounting member including an arrangement (412) releasably attaching the mounting member to the peak portion.

* * * * *